United States Patent [19]

Koenig et al.

[11] 4,104,298

[45] Aug. 1, 1978

[54] MANUFACTURE OF SULFAMIC ACID HALIDES

[75] Inventors: Karl-Heinz Koenig, Frankenthal; Gerhard Hamprecht, Mannheim, both of Germany

[73] Assignee: BASF Aktiengesellschaft, Ludwigshafen of Germany

[21] Appl. No.: 669,467

[22] Filed: Mar. 23, 1976

[30] Foreign Application Priority Data

Apr. 5, 1975 [DE] Fed. Rep. of Germany ....... 2514937

[51] Int. Cl.$^2$ .......................................... C07C 139/00
[52] U.S. Cl. ................................................ 260/543 R
[58] Field of Search ................................... 260/543 R

[56] References Cited

U.S. PATENT DOCUMENTS

| | | | |
|---|---|---|---|
| 3,706,794 | 12/1972 | Homer | 260/543 R |
| 3,795,705 | 3/1974 | Chan | 260/543 R |
| 3,857,841 | 12/1974 | Keil | 260/543 R |

FOREIGN PATENT DOCUMENTS

| | | | |
|---|---|---|---|
| 2,164,176 | 6/1973 | Fed. Rep. of Germany | 260/543 |
| 1,405,639 | 9/1975 | United Kingdom | 260/543 R |

*Primary Examiner*—Norman Morgenstern
*Attorney, Agent, or Firm*—Keil, Thompson & Shurtleff

[57] ABSTRACT

Sulfamic acid halides are produced by reaction of sulfamic acids with phosphorus pentahalide in the presence of phosphorus oxyhalide in specific molar ratios and in the presence of halohydrocarbons. The products, some of which are new compounds, are starting materials for the manufacture of plant protection agents, dyes and pharmaceuticals.

10 Claims, No Drawings

MANUFACTURE OF SULFAMIC ACID HALIDES

The present invention relates to a new process for the manufacture of sulfamic acid halides by reaction of sulfamic acids with phosphorus pentahalide in the presence of phosphorus oxyhalide, in specific molar ratios, and in the presence of halohydrocarbons, and to new sulfamic acid halides.

German Published Application No. 2,164,176 discloses the manufacture of sulfamic acid halides by reaction of sulfamic acids with an acid halide of sulfurous acid, phosphoric acid, phosphorous acid, carbonic acid or oxalic acid. Thionyl chloride, thionyl bromide, phosphorus pentachloride, phosphorus trichloride, phosphorus oxychloride, phosphorus pentabromide, phosphorus tribromide, phosgene, oxalyl chloride and oxalyl bromide are disclosed as preferred acid halides. As is shown by the Examples, only one acid halide at a time is used. Other than phosgene and phosphorus pentachloride, which each occur in one Example, only thionyl chloride is illustrated as the starting halide in the remaining Examples. The said German Published Application expressly teaches that at least the stoichiometric amount of acid halide is necessary for the reaction, but that a ratio of from 1.1 to 2 moles of acid halide per mole of starting material II is preferred. The process is unsatisfactory in respect of protection of the environment if thionyl halides are used, and in respect of yield and purity of the end product if the other acid halides, e.g. phosphorus pentachloride (Example 2b), are used. If the synthesis of the end products I is carried out with thionyl chloride, 1 mole of sulfur dioxide is always formed in addition to 1 mole of hydrogen chloride per mole of sulfamic acid halide; this sulfur dioxide must be removed from the stream of off-gas and trapped by means of sodium hydroxide solution in the form of bisulfite, which must then be concentrated and dumped. Furthermore, the separation of the excess thionyl chloride, used in the reaction, from the chlorohydrocarbons which are preferred as solvents proves difficult because the difference in boiling point is in most cases slight.

It is an object of the present invention to provide a new process by which sulfamic acid halides can be manufactured more simply and more economically, in better yield and greater purity.

A further object of the present invention is to provide new sulfamic acid halides.

We have found that these objects are achieved and that sulfamic acid halides of the formula

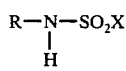
    I where R is an aliphatic or cycloaliphatic radical and X is halogen, are obtained in an advantageous manner by reaction of sulfamic acids of the formula

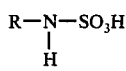
    II where R has the above meanings, of their metal salts, with an acid halide in the presence of a solvent, if the reaction is carried out with a phosphorus pentahalide as the acid halide in an amount of from 0.35 to 0.6 mole, per mole of starting material II, in the presence of from 1 to 5 moles of phosphorus oxyhalide per mole of phosphorus pentahalide, and in the presence of from 50 to 300% by weight — based on starting material II — of a halohydrocarbon as the solvent.

Further, we have found that the process may be carried out advantageously if, in a first stage, an isocyanate of the formula

    III where R has the above meanings is reacted with sulfuric acid to give a sulfamic acid of the formula

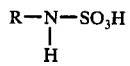
    II where R has the above meanings and thereafter, in a second stage, the compound II or its metal salt is reacted with from 0.35 to 0.6 mole, per mole of starting material II, of a phosphorus pentahalide as the acid halide, in the presence of from 1 to 5 moles of phosphorus oxychloride, per mole of phosphorus pentahalide, and in the presence of from 50 to 300% by weight — based on starting material II — of a halohydrocarbon as the solvent, to give the end product I.

Where ethylsulfamic acid is used, the reaction can be represented by the equation:

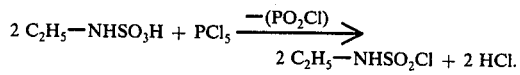

Compared to the conventional process using sulfur-free halides, the process of the invention gives sulfamic acid halides more simply and more economically, in better yield and greater purity. Compared to reactions with thionyl halides, the yield and purity are as good or better, but the essential advantage of the process of the invention resides in greater ease of working up, reduced problems in dealing with the off-gas and effluent, and hence better protection of the environment. All these advantageous results are surprising in view of the prior art, since it was not to be expected that, in the solvent according to the invention, it is necessary to use mixtures of specific amounts of the two acid halides, and in particular neither excess amounts nor stoichiometric amounts, but substantially less than the stoichiometric amount of phosphorus pentachloride, to achieve high yields of end product. The process according to the invention is also suprising in view of U.S. Pat. No. 3,706,794 which expressly teaches the use of an excess of phosphorus pentachloride, based on starting material, for the manufacture of aromatic sulfonyl chlorides. As a result of the great saving of halogenating agent, e.g. the use of only 48 mole percent of phosphorus pentachloride as against 115 mole percent of thionyl chloride, the process of the invention is very economical. The problem of dealing with the off-gas is simplified substantially, since sulfur dioxide is no longer produced alongside the hydrogen chloride and hence it is not necessary to use expensive corrosion-resistant separation equipment. The phosphoric acid, containing chloride ions, formed as a by-product accumulates in the distillation residue and is readily water-soluble; after brief heating it is possible, e.g., to preceipitate sparingly soluble phosphates, which are inexpensive starting materials for fertilizers, from the aqueous solution by addition of metal salts, e.g. calcium salts, or ammonium salts or their mixtures. Finally, if phosphorus pentachloride and phosphorus oxychloride are used, the chlorohydrocarbons preferred as solvents can be separated substantially more easily after the reaction than when thionyl chloride is used.

Preferred starting materials II, III and, accordingly, preferred end products I are those where R is straight-chain or branched alkyl of 1 to 20 carbon atoms, especially of 1 to 8 carbon atoms, or alkyl of 2 to 20 carbon atoms, especially 2 to 8 carbon atoms, and advantageously 2 to 6 carbon atoms, which is substituted either by a plurality of alkoxy groups, preferably 3 or 2 alkoxy groups, or, especially, by one alkoxy group, of 1 to 7 carbon atoms, especially 1 to 3 carbon atoms, or is cycloalkyl of 4 to 8 carbon atoms, and X is bromine or, in particular, chlorine. The radicals mentioned may further be substituted by groups and/or atoms which are inert under the reaction conditions, e.g. chlorine, bromine, alkyl and alkoxy each of 1 to 4 carbon atoms, carbalkoxy of 2 to 4 carbon atoms and cycloalkyl of 4 to 6 carbon atoms. Preferred starting materials II and III and end products I are especially those where R is n-hexyl, cyclopentyl, cyclohexyl, cycloheptyl, cyclobutyl, cyclooctyl, alkyl of 2 to 5 carbon atoms which is substituted by chlorine, bromine or cycloalkyl of 4 to 6 carbon atoms, branched alkyl of 3 to 7 carbon atoms, 1-methyl-1-propyl, hexyl-(3), hepthyl-(4), β-methoxyisopropyl or alkyl of 2 to 20 carbon atoms, especially 2 to 8 carbon atoms and advantageously 2 to 6 carbon atoms, which is substituted by a plurality of alkoxy groups, preferably 3 or 2 alkoxy groups, or, especially, by one alkoxy group, of 1 to 7 carbon atoms, especially 1 to 3 carbon atoms, and X is bromine or chlorine.

Examples of appropriate sulfamic acids II are methylsulfamic acid, ethylsulfamic acid, n-propylsulfamic acid, isopropylsulfamic acid, n-butylsulfamic acid, isobutylsulfamic acid, sec.-butylsulfamic acid, cyclobutylsulfamic acid, 1-ethyl-1-propylsulfamic acid, 1,2-dimethyl-1-propylsulfamic acid, n-pentylsulfamic acid, cyclopentylsulfamic acid, n-hexylsulfamic acid, hexyl-(3)-sulfamic acid, cyclohexylsulfamic acid, cycloheptylsulfamic acid, hepthyl-(4)-sulfamic acid, cyclooctylsulfamic acid, 2-methyl-1-ethyl-1-propylsulfamic acid, 1,2,2-trimethyl-1-propylsulfamic acid, 1,3-dimethyl-1-n-butylsulfamic acid, 1,2-dimethyl-1-n-butylsulfamic acid, 1,2-dimethyl-1-n-hexylsulfamic acid, 1-cyclohexyl-1-ethylsulfamic acid, 2-chloroisopropylsulfamic acid, 2-chloropropylsulfamic acid, 3-chloropropylsulfamic acid, 3-bromopropylsulfamic acid and 1-chloromethyl-1-propylsulfamic acid; tert.-butyl-, pentyl-(2)-, n-heptyl-, n-octyl-, n-nonyl-, n-decyl-, 2-ethylhexyl-, 2-ethylpentyl-, 3-ethylpentyl-, 2,3-dimethyl-n-butyl-, 2-methylpentyl-, 3-methylpentyl-, 2-methylheptyl-, 3-methylheptyl-, 4-methylheptyl-, 3-ethylhexyl-, 2,3-dimethylhexyl-, 2,4-dimethylhexyl-, 2,5-dimethylhexyl-, undecyl-, dodecyl-, tridecyl-, tetradecyl-, pentadecyl-, hexadecyl-, heptadecyl-, octadecyl-, nonadecyl- and eicosyl-sulfamic acid; the ω-methoxy-, ω-ethoxy-, ω-n-propoxy-, ω-isopropoxy-, ω-n-butoxy-, ω-isobutoxy-, ω-sec.-butoxy-, ω-tert.-butoxy-, ω-pentoxy-, ω-pentoxy-(2)-, ω-pentoxy-(3)-, ω-n-hexoxy- and ω-n-heptoxy- derivatives of ethyl-, n-propyl-, isopropyl-, n-butyl-, isobutyl-, sec.-butyl-, tert.-butyl-, pentyl-, pentyl-(2)-, pentyl-(3)-, n-hexyl-, n-heptyl-, n-octyl-, n-nonyl-, n-decyl-, 2-ethylhexyl-, 2-ethylpentyl- 3-ethylpentyl-, 2,3-dimethyl-n-butyl-, 2-methylpentyl-, 3-methylpentyl-, 2-methylheptyl-, 3-methylheptyl-, 4-methylheptyl-, 3-ethylhexyl-, 2,3-dimethylhexyl-, 2,4-dimethylhexyl-, 2,5-dimethylhexyl-, undecyl-, dodecyl-, tridecyl-, tetradecyl-, pentadecyl-, hexadecyl-, heptadecyl-, octadecyl-, nonadecyl- and eicosylsulfamic acid; corresponding methyl, ethyl, n-propyl, isopropyl, n-butyl, isobutyl, sec.-butyl, tert.-butyl, pentyl, pentyl-(2)-, pentyl-(3)-, n-hexyl and n-heptyl ethers of n-propyl-, isopropyl-, n-butyl-, isobutyl-, sec.-butyl-, tert.-butyl-, pentyl-, pentyl-(2)-, pentyl-(3)-, n-hexyl-, n-heptyl-, n-octyl-, n-nonyl-, n-decyl-, 2-ethylhexyl-, 2-ethylpentyl-, 3-ethylpentyl-, 2,3-dimethyl-n-butyl-, 2-methylpentyl-, 3-methylpentyl-, 2-methylheptyl-, 3-methylheptyl-, 4-methylheptyl-, 3-ethylhexyl-, 2,3-dimethylhexyl-, 2,4-dimethylhexyl-, 2,5-dimethylhexyl-, undecyl-, dodecyl-, tridecyl-, tetradecyl-, pentadecyl-, hexadecyl-, octadecyl-, nonadecyl- and eicosyl-sulfamic acid, the ether link being in the 1- or 2-position of the said acids, and of ethylsulfamic acid, the ether link being in the 1-position thereof.

The starting materials II can be used in the form of sulfamic acids, preferably of the sulfamic acids, free from sulfuric acid, which have been manufactured by the process described in German Published Application No. 2,164,197, or of their metal salts. Preferred metal salts are the alkali metal salts or alkaline earth metal salts, e.g. magnesium, calcium, lithium, potassium and especially sodium sulfamates.

The phosphorus pentahalides and phosphorus oxyhalides used are advantageously the bromides and preferably the chlorides. The reaction is carried out with from 0.35 to 0.6, preferably from 0.4 to 0.5, mole of phosphorus pentahalide, based on starting material II, and in the presence of from 50 to 300% by weight, preferably from 100 to 200% by weight — based on starting material II — of a halo-hydrocarbon as the solvent, and of from 1 to 5 moles, preferably from 2 to 4 moles, of phosphorus oxyhalide per mole of phosphorus pentahalide. The phosphorus oxyhalide added serves as a solvent in the process according to the invention. Suitable halohydrocarbons which are inert under the reaction conditions are, in particular, chlorohydrocarbons, e.g. tetrachloroethylene, 1,1,2,2- and 1,1,1,2- tetrachloroethane, amyl chloride, cyclohexyl chloride, dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, 1,1,1- and 1,1,2-trichloroethane, trichloroethylene, pentachloroethane, 1,2-cis-dichloroethylene, 1,2-dichloroethane, 1,1-dichloroethane, n-propyl chloride, n-butyl chloride, 2-, 3- and iso-butyl chloride, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,10-dibromodecane, 1,4-dibromobutane and corresponding mixtures. It is advantageous to use from 20 to 1,000% by weight, preferably from 35 to 300% by weight, and especially from 65 to 150% by weight — based on phosphorus oxyhalide — of the halohydrocarbon.

The reaction is as a rule carried out at from −10° to 130° C, preferably from 10° to 120° C, and especially from 60° to 100° C, under atmospheric or superatmospheric pressure, continuously or batchwise. It may be carried out as follows: a mixture of starting material II, acid halide, phosphorus oxyhalide and solvent is kept at the reaction temperature for from 3 to 8 hours. The acid chloride or the starting material II may first be mixed with the solvent, after which the other component is added. The end product I is isolated from the reaction mixture by conventional methods, e.g. by fractional distillation. In an example of an advantageous embodiment, a suspension of the sulfamic acid in one of the above halohydrocarbons is mixed with the appropriate amount of phosphorus oxychloride and the phosphorus pentachloride is then added by means of a metering device. However, it is also possible to suspend the phosphorus pentachloride in the phosphorus oxychloride and then to run this mixture into the suspension of the sulfamic acid in one of the above inert halohydrocarbons. Instead of the phosphorus pentachloride, its starting materials can advantageously be used. For example, following the process of U.S. Pat. No. 1,906,440, the calculated amount of chlorine is run into a solution of phosphorus trichloride in phosphorus oxychloride, and this suspension is then run into the suspension of the sulfamic acid in one of the above inert halohydrocarbons. However, according to a procedure from the same patent, it is also possible to add the calculated amount of chlorine to a mixture of yellow phosphorus in phosphorus oxychloride and then introduce the whole into the suspension of the sulfamic acid.

In an advantageous embodiment, the reaction mixture from the manufacture of the starting material II is used, without isolation of the latter, as the starting mixture for the process according to the invention, if appropriate after addition of halohydrocarbons. Preferably, the reaction mixture described in German Published Application No. 2,164,197 is used as the starting mixture. This mixture is obtained on reaction of isocyanate with anhydrous sulfuric acid at not less than 25° C in an inert solvent, e.g. in one of the above halohydrocarbons. The following procedure is preferred: a mixture of starting material III and solvent, on the one hand, and sulfuric acid or a mixture of sulfuric acid and solvent, on the other, are introduced simultaneously but separately, with vigorous stirring, into a receiver containing solvent. The addition suitably takes from 10 to 55 minutes and is frequently carried out at from 25° to 50° C, after which the reaction is carried out at not less than 50° C. Advantageously, the solvents used are the halohydrocarbons which are also used for the process according to the invention. Advantageously, the phosphorus oxyhalide and, if appropriate, a further amount of solvent, is not added and the reaction according to the invention is carried out, in this second stage, in the course of from 3 to 8 hours. If appropriate, the reaction temperature is further varied within the above temperature range, e.g. raised to from 60° to 120° C, especially from 80° to 120° C. The end product I is isolated in the manner described above.

The compounds which may be manufactured by the process of the invention are valuable starting materials for the manufacture of plant protection agents, dyes and pharmaceuticals. Thus, e.g., the o-sulfamidobenzoic acids described in German Published Application No. 2,104,682 may be manufactured from them by reaction with anthranilic acid or its salts. Cyclization of these compounds, e.g. by the process described in German Published Application No. 2,105,687, gives the 2,1,3-benzothiadiazin-4-one-2,2-dioxides, the use of which as and for plant protection agents and pharmaceuticals is described in the same reference. The very good herbicidal properties of this category of compounds are described in U.S. Pat. No. 3,621,017, German Patent No. 1,937,551 and German Published Application No. 2,131,401.

Their use as important intermediates for herbicides is furthermore dealt with in German Pat. No. 1,542,836 and German Patent Application No. P 23 49 114.7; furthermore, reaction of alkylaminosulfonyl chlorides with sulfenyl chlorides by the process of German Pat. No. 1,953,356 gives intermediates for fungicides.

Reaction of the end products I with substituted glycollic acid analides gives further herbicides (German Published Application No. 2,201,432 and German Published Application No. 2,310,757).

Finally, the 2,1,3-benzothiadiazin(4)one-2,2-dioxides obtainable from N-alkylaminosulfonyl chlorides have valuable pharmacological properties. Thus, U.S. Pat. No. 3,041,336 discloses that 3-oxo-1,2,6-thiadiazine-1,1-dioxides may be used as antiphlogistics, antipyretics and analgesics. Biological applications are described in Examples 8 and 9.

Sulfamic acid halides of the general formula

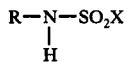

$$R-N-SO_2X \qquad \qquad I$$
$$\underset{H}{|}$$

where R and X have the above preferred meanings, are particularly suitable in this context. Particularly advantageous end products I for the above applications are those where R is straight-chain or branched alkyl of 1 to 8 carbon atoms, cycloheptyl, cyclohexyl, cyclobutyl, cyclopentyl, cyclooctyl, alkyl of 2 to 5 carbon atoms which is substituted by chlorine, bromine or cycloalkyl of 4 to 6 carbon atoms, 1-methyl-1-propyl, hexyl-(3), heptyl-(4), β-methoxy-isopropyl or alkyl of 2 to 20 carbon atoms, especially 2 to 8 carbon atoms and advantageously 2 to 6 carbon atoms which is substituted by 3, 2 or, especially, 1 alkoxy group of 1 to 7 carbon atoms, especially 1 to 3 carbon atoms, and X is chlorine or bromine. Specifically, methyl-, ethyl-, n-propyl-, isopropyl-, n-butyl-, isobutyl-, pentyl-3-, cyclopentyl- cyclohexyl-, n-hexyl-, 1,2-dimethyl-1-n-propyl-, 1,2-dimethyl-1-n-butyl-, 1,3-dimethyl-1-n-butyl-, cycloheptyl-, 1,2-dimethyl-1-n-hexyl-, 2-chloroisopropyl- and 2-chloropropylsulfamic acid chloride are preferred compounds for the above applications.

In the Examples, parts are by weight.

EXAMPLE 1

(a) 54.2 parts of phosphorus pentachloride are introduced by means of a metering device into a suspension of 69.5 parts of isopropylsulfamic acid in 134 parts of phosphorus oxychloride and 100 parts of 1,2-dichloroethane at 0° C, whilst stirring. The reaction mixture is then heated to 95° C in the course of 30 minutes and is stirred for 6½ hours at from 95° to 98° C. The mixture is now subjected to fractional distillation. 67.7 parts (86% of theory) of isopropylsulfamic acid chloride of boiling point 78°-83° C/0.1-0.3 mm Hg and $n_D^{25} = 1.4569$ are obtained.

(b) The following yields of isopropylsulfamic acid chloride are obtained by the method described in Example 1(a), but adding 49 parts of phosphorus pentachloride and varying the solvent mixture.

TABLE 1

| POCl$_3$ (parts) | ClCH$_2$—CH$_2$Cl (parts) | Isopropylsulfamic acid chloride (yield in % of theory) |
|---|---|---|
| 134 | 100 | 74 |
| 100 | 125 | 76 |

EXAMPLE 2

(a) 18.4 parts of chlorine are passed into a mixture of 35.7 parts of phosphorus trichloride in 134 parts of phosphorus oxychloride whilst stirring at from 20° to 40° C. The suspension formed is now added, in the course of 10 minutes, to a suspension of 69.5 parts of isopropylsulfamic acid in 100 parts of 1,2-dichloroethane at 60° C, whilst stirring. The reaction mixture is then stirred for 6 hours at from 95° to 98° C, after which it is freed from 1,2-dichloroethane and phosphorus oxychloride under reduced pressure. Distillation of the residue gives 65.7 parts (84% of theory) of isopropylsulfamic acid chloride of boiling point 78°–83° C/0.1–0.3 mm Hg and $n_D^{25} = 1.4569$.

(b) If the reaction is carried out under the same conditions with 100 parts of 1,1,2-trichloroethane, 64 parts (81% of theory) of isopropylsulfamic acid chloride are obtained.

EXAMPLE 3

42.5 parts of isopropyl isocyanate and 50 parts of oleum (2% by weight of $SO_3$) are run simultaneously, through 2 separate inlets, into 160 parts of 1,2-dichloroethane at from 25° to 35° C, whilst stirring. The mixture is then stirred for 15 minutes at 84° C. After distilling off 20 parts of 1,2-dichloroethane, a suspension of 54.2 parts of phosphorus pentachloride in 100 parts of phosphorus oxychloride is added in the course of 10 minutes and the batch is then stirred for 6 hours at from 95° to 98° C. After removing the solvent under reduced pressure, distillation of the residue gives 65 parts (83% of theory) of isopropylsulfamic acid chloride of boiling point 75°–82° C/0.2 mm Hg and $n_D^{25} = 1.4560$.

EXAMPLE 4

54.2 parts of phosphorus pentachloride are added in portions to 89.6 parts of cyclohexylsulfamic acid, suspended in a mixture of 113 parts of 1,2-dichloroethane and 134 parts of phosphorus oxychloride, at 20° C, whilst stirring. The reaction mixture is then heated to 95° C in the course of 30 minutes and is stirred at from 95° to 98° C for 7½ hours. After removing the solvent under reduced pressure distillation of the residue gives 94 parts (95% of theory) of cyclohexylsulfamic acid chloride of boiling point 103°–111° C/0.05 mm Hg (melting point 42°–44°).

EXAMPLE 5

(a) 77.2 parts of phosphorus pentachloride in 80 parts of phosphorus oxychloride are introduced, in the course of 7 minutes, into a solution of 121 parts of β-methoxyisopropylsulfamic acid in 180 parts of 1,2-dichloroethane at 20° C, whilst stirring. The reaction mixture is heated to 85° C in the course of ½ hour and is then stirred for 3 hours at from 85° to 90° C. Thereafter the reaction solution is concentrated under reduced pressure and the residue is distilled on a thin film evaporator. 62.4 parts (47% of theory) of β-methoxyisopropylsulfamic acid chloride, of $n_D^{25} = 1.4650$, are obtained at a bath temperature of 125° C and at 0.01 mm Hg.

(b) Manufacture of the sulfamic acid: 1,000 parts of methoxyacetone in a solution of 632 parts of hydroxylamine hydrochloride in 5,200 parts of 10 percent strength by weight sodium carbonate solution are stirred for 24 hours at 22° C. After extracting the aqueous phase with 2,000 parts of methylene chloride, and drying and concentrating the extract, the methoxy-acetone-oxime is obtained as a yellowish viscous oil. 600 parts thereof are dissolved in 2,000 parts of toluene and converted by means of 145 parts of hydrogen chloride gas, in the course of one hour, into the hydrochloride, which is filtered off and washed with petroleum ether. 139.5 parts of the methoxyacetone-oxime hydrochloride thus obtained, in 500 parts of isopropanol, are hydrogenated in the course of 5 hours at 35° C and a hydrogen pressure of 22 atmospheres, over 40 parts of an 0.5% strength by weight platinum-on-graphite catalyst. The reaction solution is filtered off and neutralized with 30 percent strength by weight sodium methylate solution. After filtering off, and concentrating the filtrate, the methoxyisopropylhydroxylamine is obtained as a yellowish oil. 98 parts thereof, dissolved in 750 parts of 1,2-dichloroethane, are saturated with a stream of sulfur dioxide in the course of 45 minutes at 20° C. After concentrating the mixture, methoxyisopropylsulfamic acid is obtained as a yellowish oil.

EXAMPLE 6

54.2 parts of phosphorus pentachloride are added in portions, in the course of 15 minutes, to 69.5 parts of isopropylsulfamic acid, suspended in 268 parts of phosphorus oxychloride, at 0° C, whilst stirring. The reaction mixture is stirred for 6½ hours at from 98 to 100° C and then freed from excess phosphorus oxychloride under reduced pressure. Subsequent distillation gives 47 parts (60% of theory) of isopropylsulfamic acid chloride of boiling point 76°–80°/0.2 mm Hg, $n_D^{25} = 1.4572$.

EXAMPLE 7

Following the procedure of U.S. Pat. No. 1,906,440, 7.42 parts of yellow phosphorus are reacted with 42.5 parts of chlorine in 134 parts of phosphorus oxychloride at from 30° to 50° C. 69.5 parts of isopropylsulfamic acid in 110 parts of 1,2-dichloroethane are then introduced into the resulting suspension of phosphorus pentachloride in the course of 1 hour, at 90° C. The reaction mixture is then stirred for 4½ hours at 92°–97° C. After removing 240 parts of solvent under reduced pressure, distillation of the residue gives 65.9 parts (84% of theory) of isopropylsulfamic acid chloride of boiling point 72°–77° C/0.1 mm Hg and $n_D^{25} = 1.4561$.

EXAMPLE 8

A suspension of 64.5 parts of sodium salt of isopropylsulfamic acid and 41.6 parts of phosphorus pentachloride in 35 parts of 1,2-dichloroethane and 150 parts of phosphorus oxychloride is stirred for 14 hours at 98° C. After removing the solvent under reduced pressure, distillation of the residue gives 48 parts (76% of theory) of isopropylsulfamic acid chloride of boiling point 69°–71° C/0.01 mm and $n_D^{25} = 1.4544$.

EXAMPLES 9 TO 15

The compounds listed in the Table are obtained by the method described in Example 1(a).

TABLE 2

| Example | Parts | Starting material RNHSO$_3$H R | Parts of end product | % of theory | Boiling point | $n_D^{25}$ |
|---|---|---|---|---|---|---|
| 9 | 55.6 | $CH_3$— | 53.8 | 83 | 74–77° C/0.2 mm Hg | |

TABLE 2-continued

| Example | Parts | Starting material RNHSO₃H R | Parts of end product | % of theory | Boiling point | $n_D^{25}$ |
|---------|-------|---|---|---|---|---|
| 10 | 69.5 | n-C₃H₇— | 63 | 80 | 73-76° C/0.1 mm Hg | |
| 11 | 76.6 | i-C₄H₉— | 68.7 | 80 | 94-96° C/0.01 mm Hg | 1.4618 |
| 12 | 93.9 | Cl—CH₂\\CH—  /  C₂H₅ | 48.5 | 47 | 104-114° C/0.4 mm Hg | 1.4889 |
| 13 | 54.3 | -n-C₆H₁₃— | 50.3 | 85 | 130° C/0.1 mm Hg$^a$ | 1.4610 |
| 14 | 91 | C₂H₅\\CH$^b$ / n-C₃H₇ | 53.8 | 54 | 130° C/0.1 mm Hg$^a$ | 1.4661 |
| 15 | 97.6 | (n-C₃H₇)₂CH—$^c$ | 49.2 | 46 | 160° C/0.1 mm Hg$^a$ | 1.4585 |

$^a$Bath temperature of the thin film evaporator
$^b n_D^{25} = 1.4690$
$^c n_D^{25} = 1.4660$, prepared according to German Published Application 2,164,197

EXAMPLE 16 (Use)

Using the procedure of German Patent Application No. P 23 57 063.0, β-methoxyisopropylsulfamic acid chloride is reacted with anthranilic acid methyl ester in the presence of triethylamine to give 3-β-methoxyisopropyl-2,1,3-benzothiadiazin(4)one-2,2-dioxide of melting point 100° C (with decomposition).

EXAMPLE 17 (Use)

In a greenhouse, plants of rice (*Oryza sativa*), Indian corn (*Zea mays*), soy (*Glycine max.*), wheat (*Triticum aestivum*), barley (*Hordeum vulgare*) and rye (*Secale ureale*), heavily infested with the weeds charlock (*Sinapis arvensis*) and yellow nutsedge (*Cyperus esculentus*) are treated, when they have grown to a height of from 3 to 23 cm, with 4 kg/ha of the active ingredient 3-β-methoxyisopropyl-2,1,3-benzothiadiazin(4)one-2,2-dioxide, dispersed or emulsified in 500 liters of water per hectare. After from 2 to 3 weeks it is found that the active ingredient is very well tolerated by the crop plants, whilst showing a good herbicidal action. The test results may be seen from the Table which follows.

Crop plants:
 Oryza sativa — 0
 Zea mays — 0
 Glycine max. — 0
 Triticum aestivum — 0
 Hordeum vulgare — 0
 Secale ureale — 0 undesired plants:
 Sinapis arvensis — 100
 Cyperus esculentus — 90
 0 = no damage
 100 = total destruction

EXAMPLE 18 (Use)

In a greenhouse, test pots are filled with loamy sandy soil and sown with seeds of rice (*Oryza sativa*) and charlock (*Sinapis arvensis*). Immediately thereafter, a treatment is carried out with the active compound 3-β-methoxyisopropyl-2,1,3-benzothiadiazin(4)one-2,2-dioxide, using 5 kg/ha of active substance, dispersed or emulsified in 500 liters of water per hectare. After from 4 to 5 weeks it is found that the active compound is very well tolerated by the crop plant, but exhibits a powerful herbicidal action. The test results may be seen from the Table which follows:

Crop plant
 Oryza sativa — 0 undesired plant
 Sinapis arvensis — 100
 0 = no damage
 100 = total destruction.

We claim:
1. A process for the manufacture of sulfamic acid halides of the formula

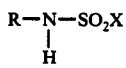   I where R is an aliphatic or cycloaliphatic radical and X is halogen, which comprises: reacting sulfamic acids of the formula

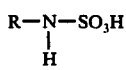   II where R has the above meanings, or their metal salts, with an acid halide in the presence of a solvent, wherein the reaction is carried out with a phosphorus pentahalide as the acid halide in an amount of from 0.35 to 0.6 mole, per mole of starting material II, in the presence of from 1 to 5 moles of phosphorus oxyhalide per mole of phosphorus pentahalide, and in the presence of from 50 to 300% by weight — based on starting material II — of a halohydrocarbon as the solvent.

2. A process as claimed in claim 1, wherein the reaction is carried out with from 0.4 to 0.5 mole of phosphorus pentahalide, based on starting material II.

3. A process as claimed in claim 1, wherein the reaction is carried out with from 100 to 200% by weight — based on starting material II — of a halohydrocarbon as the solvent.

4. A process as claimed in claim 1, wherein the reaction is carried out with from 2 to 4 moles of phosphorus oxyhalide per mole of phosphorus pentahalide.

5. A process as claimed in claim 1, wherein the reaction is carried out with tetrachloroethylene, 1,1,2,2- or 1,1,1,2-tetrachloroethane, amyl chloride, cyclohexyl chloride, dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, 1,1,1- and 1,1,2-trichloroethane, trichloroethylene, pentachloroethane, 1,2-cis-dichloroethylene, 1,2-dichloroethane, 1,1-dichloroethane, n-propyl chloride, n-butyl chloride, 2-, 3- and iso-butyl chloride, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,10-dibromodecane, 1,4-dibromobutane or mixtures thereof.

6. A process as claimed in claim 1, wherein the reaction is carried out with from 20 to 1,000% by weight of halohydrocarbon, based on phosphorus oxyhalide.

7. A process as claimed in claim 1, wherein the reaction is carried out with from 35 to 300% by weight of halohydrocarbon, based on phosphorus oxyhalide.

8. A process as claimed in claim 1, wherein the reaction is carried out at from −10° to 130° C.

9. A process as claimed in claim 1, wherein the reaction is carried out at from 10° to 120° C.

10. A process as claimed in claim 1 wherein R is isopropyl, X is Cl and said phosphorous pentahalide is phosphorous pentachloride, said phosphorous oxyhalide is phosphorous oxychloride, and said halohydrocarbon is 1,2-dichloroethane.

* * * * *